United States Patent [19]
Odell et al.

[11] Patent Number: 5,769,841
[45] Date of Patent: Jun. 23, 1998

[54] ELECTROSURGICAL APPARATUS FOR LAPAROSCOPIC AND LIKE PROCEDURES

[75] Inventors: Roger C. Odell, Louisville; Paul H. Emerling, Nederland; David W. Newton, Boulder; Robert C. Steinway, Boulder; Don R. Boyle, Boulder, all of Colo.

[73] Assignee: Electroscope, Inc., Boulder, Colo.

[21] Appl. No.: 489,934

[22] Filed: Jun. 13, 1995

[51] Int. Cl.⁶ .................................................. A61B 17/39
[52] U.S. Cl. ................................ 606/1; 606/52; 606/205
[58] Field of Search ........................ 606/41, 42, 45–52, 606/205–208, 1

[56] References Cited

U.S. PATENT DOCUMENTS

| | | |
|---|---|---|
| 984,756 | 2/1911 | Frisch . |
| 1,754,806 | 4/1930 | Stevenson . |
| 2,004,559 | 6/1935 | Wappler et al. . |
| 2,008,367 | 7/1935 | Rhinevault . |
| 2,448,741 | 9/1948 | Scott et al. . |
| 2,741,248 | 11/1956 | Woodhall . |
| 3,070,132 | 4/1962 | Sheridan . |
| 3,580,983 | 5/1971 | Jackson . |
| 3,585,985 | 6/1971 | Gould . |
| 3,601,126 | 8/1971 | Estes . |
| 3,706,008 | 12/1972 | Kremer . |
| 3,707,149 | 12/1972 | Hao et al. . |
| 3,804,096 | 4/1974 | Gonser . |
| 3,834,392 | 9/1974 | Lampman et al. . |
| 3,838,242 | 9/1974 | Goucher . |
| 3,895,635 | 7/1975 | Justus et al. . |
| 3,898,991 | 8/1975 | Ikuno et al. . |
| 3,905,373 | 9/1975 | Gonser . |
| 3,933,157 | 1/1976 | Bjurwill et al. . |
| 3,946,738 | 3/1976 | Newton et al. . |
| 3,963,856 | 6/1976 | Carlson et al. . |
| 3,994,287 | 11/1976 | Turp et al. . |
| 4,003,380 | 1/1977 | Wien . |
| 4,084,594 | 4/1978 | Mosior . |
| 4,181,131 | 1/1980 | Ogiu . |
| 4,184,492 | 1/1980 | Meinke et al. ............................ 606/46 |
| 4,200,104 | 4/1980 | Harris . |
| 4,231,372 | 11/1980 | Newton . |
| 4,237,887 | 12/1980 | Gonser . |
| 4,248,716 | 2/1981 | La Valley . |
| 4,303,073 | 12/1981 | Archibald . |
| 4,311,144 | 1/1982 | Harada . |
| 4,325,374 | 4/1982 | Komiya . |
| 4,367,746 | 1/1983 | Derechinsky . |

(List continued on next page.)

FOREIGN PATENT DOCUMENTS

| | | |
|---|---|---|
| 3013784 | 4/1980 | Germany . |

*Primary Examiner*—Michael Peffley
*Attorney, Agent, or Firm*—Sixbey, Friedman, Leedom & Ferguson, P.C.; Gerald J. Ferguson, Jr.; Eric J. Robinson

[57] ABSTRACT

An electrosurgical instrument having a safety shield for use in laparoscopic or like electrosurgical procedures designed to receive a plurality of electrosurgical instrument inserts. The electrosurgical inserts are designed so as to provide quick and easy attachment to the electrosurgical apparatus while still providing enhanced resistance to rotation forces encountered during an electrosurgical procedure, and to distribute actuation forces occurring during use. The safety shield includes a crimped portion for transferring forces that occur during operation of an articulating instrument inserted therein to a handle assembly of the electrosurgical instrument. The electrosurgical instrument has a seal that reduces or prevents electrical current from flowing between the active electrode and shield assemblies. The electrosurgical instrument further includes a connector assembly for receiving a mating cable connector and providing a fail-safe interconnection therewith. A second preferred embodiment of the electrosurgical instrument is adapted to be removably connected with a replaceable shield/connector assembly through which the instrument is inserted. Furthermore, position of the shield with respect to the electrosurgical instrument can easily be accomplished.

16 Claims, 14 Drawing Sheets

U.S. PATENT DOCUMENTS

| | | |
|---|---|---|
| 4,374,517 | 2/1983 | Hagiwara . |
| 4,433,687 | 2/1984 | Burke et al. . |
| 4,440,170 | 4/1984 | Golden et al. . |
| 4,449,532 | 5/1984 | Storz . |
| 4,494,541 | 1/1985 | Archibald . |
| 4,601,710 | 7/1986 | Moll . |
| 4,615,330 | 10/1986 | Nagasaki et al. . |
| 4,617,927 | 10/1986 | Manes . |
| 4,618,885 | 10/1986 | Nagasaki et al. . |
| 4,638,802 | 1/1987 | Okada . |
| 4,662,369 | 5/1987 | Ensslin . |
| 4,674,501 | 6/1987 | Greenberg . |
| 4,716,897 | 1/1988 | Noguchi et al. . |
| 4,744,361 | 5/1988 | Karaswa . |
| 4,844,063 | 7/1989 | Clark . |
| 4,886,505 | 12/1989 | Haynes et al. . |
| 4,919,129 | 4/1990 | Weber, Jr. et al. . |
| 4,983,456 | 1/1991 | Iwaskow et al. . |
| 5,009,643 | 4/1991 | Reich et al. . |
| 5,087,257 | 2/1992 | Farin et al. . |
| 5,116,353 | 5/1992 | Green . |
| 5,147,357 | 9/1992 | Rose et al. ................................ 606/51 |
| 5,176,702 | 1/1993 | Bales et al. . |
| 5,263,967 | 11/1993 | Lyons, III et al. . |
| 5,275,615 | 1/1994 | Rose ....................................... 606/207 |
| 5,277,696 | 1/1994 | Hagen . |
| 5,295,993 | 3/1994 | Green . |
| 5,308,358 | 5/1994 | Bond et al. ............................. 606/205 |
| 5,312,401 | 5/1994 | Newton et al. .......................... 606/46 |
| 5,334,198 | 8/1994 | Hart et al. ................................ 606/52 |
| 5,344,428 | 9/1994 | Griffiths . |
| 5,431,638 | 7/1995 | Hennig et al. . |
| 5,571,137 | 11/1996 | Marlow et al. ........................ 606/207 |

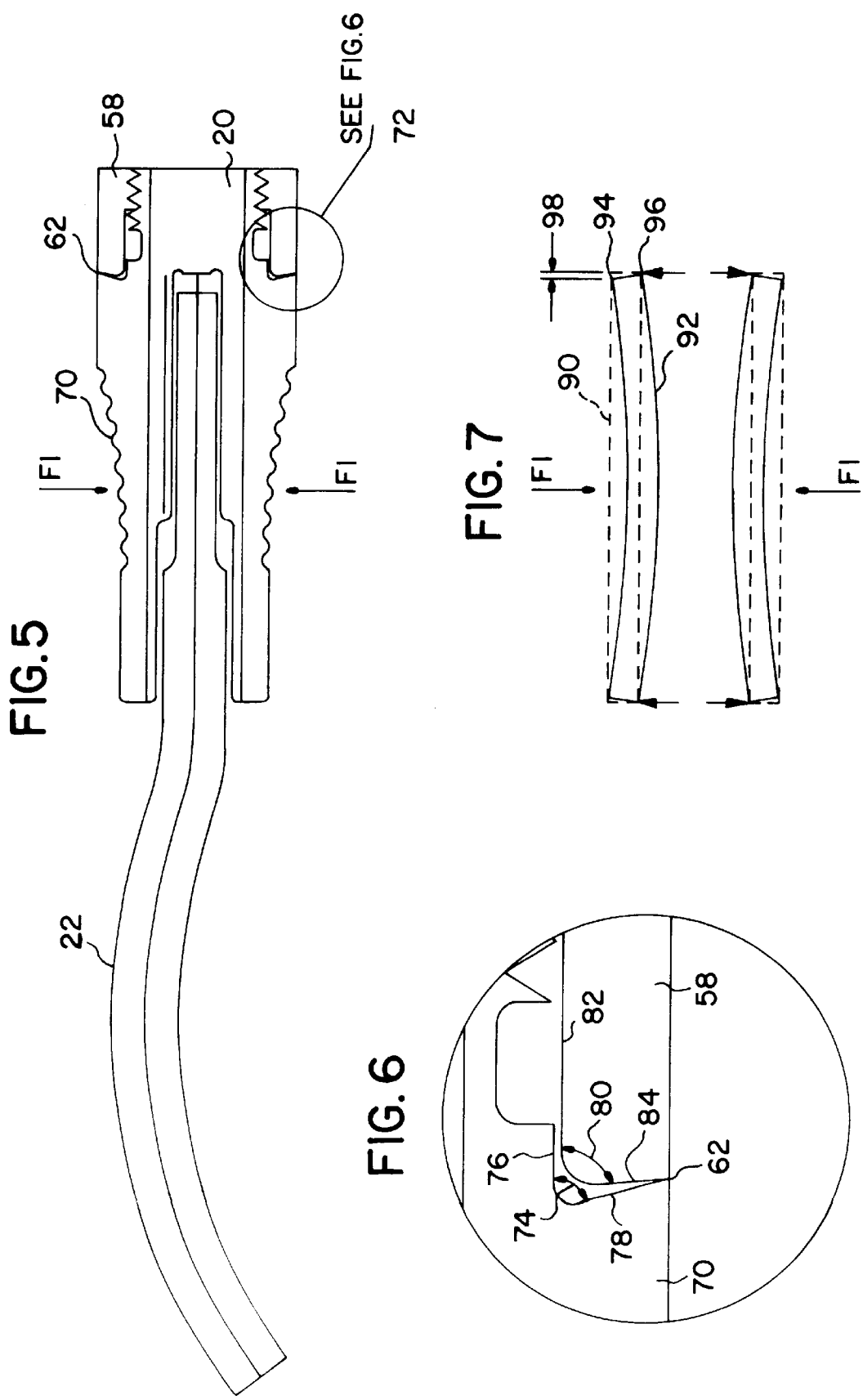

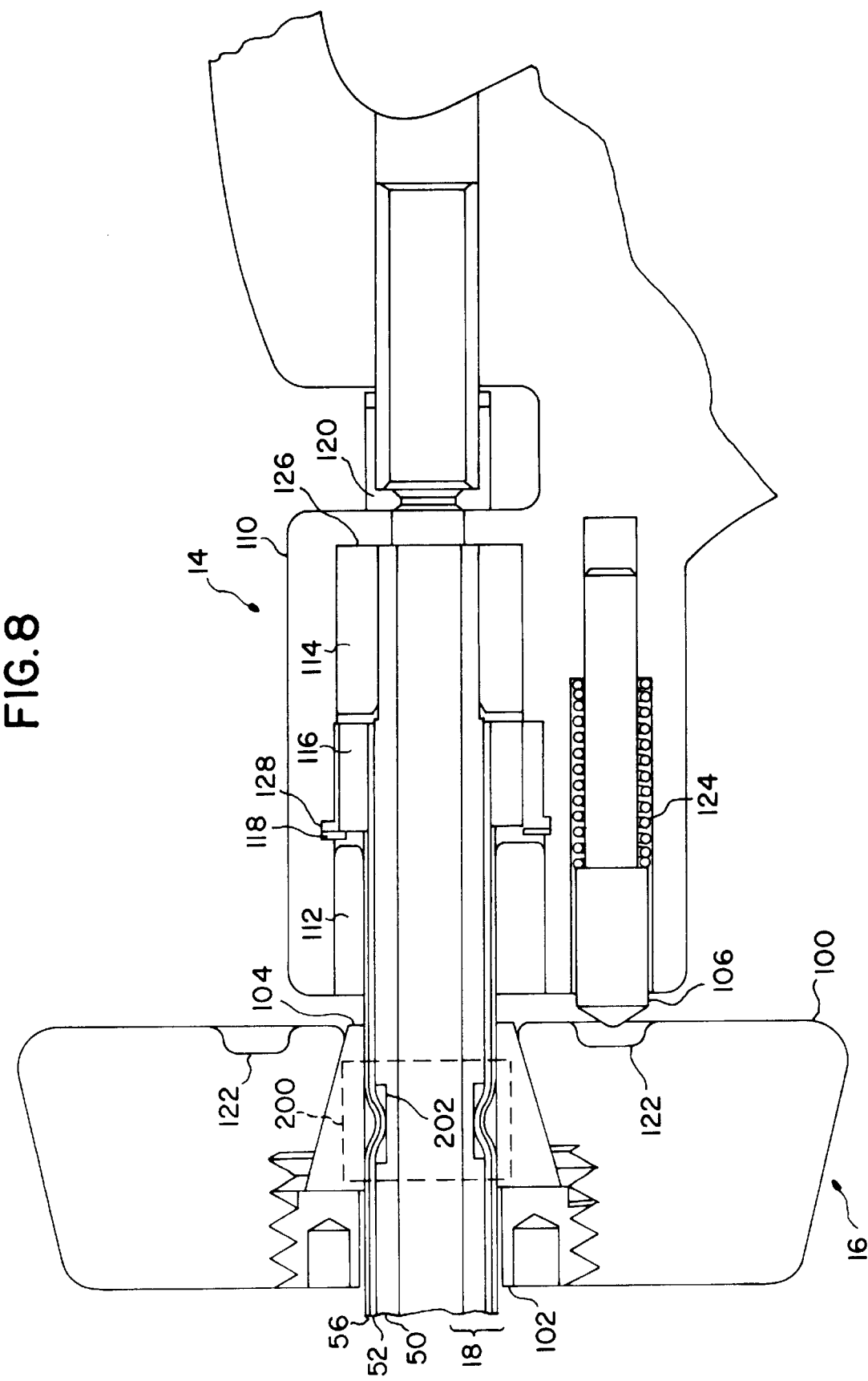

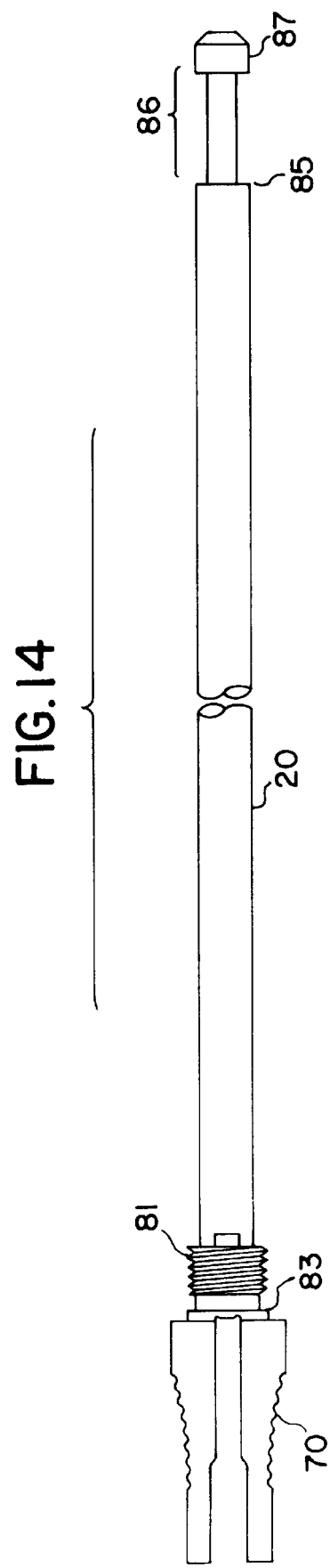

ELECTROSURGICAL APPARATUS FOR LAPAROSCOPIC AND LIKE PROCEDURES

BACKGROUND OF THE INVENTION

This invention relates to electrosurgical apparatus and in particular to such apparatus for performing laparoscopic, pelvoscopic, arthroscopic, thoroscopic and the like surgical procedures. Procedures of the foregoing type are experiencing explosive growth in that incisions are kept to a minimum size and thus such procedures facilitate shorter hospital stays and lower costs. For example, with laparoscopic surgery, a patient can return to normal activity within about one week, whereas with procedures where a large incision is made, about a month for full recovery may be required. It is to be understood that hereinafter and in the claims, whenever the term "laparoscopic" is employed, similar procedures such as pelvoscopic, arthroscopic, thoroscopic, and the like where small incisions of the foregoing type are made are also encompassed by this term.

Prior art electrosurgical laparoscopic apparatus typically include an active electrode probe that is removably insertable through a trocar sheath and that includes an electrode having an insulative coating thereon. The tip of the probe may be of different conventional shapes such as needle-shape, hook-shape, spatula-shape, graspers, scissors, etc. and serve various conventional functions such as suction, coagulation, irrigation, pressurized gas, cutting, etc. There are, however, various problems which may arise with respect to the use of such a prior art apparatus when used in laparoscopic or like procedures.

A first problem may arise if the insulation on the active electrode is damaged thereby allowing active current (possibly in the form of arcing) to pass therethrough directly to the patient's tissue (possibly the bowel or colon) whereby peritonitis may set in within several days. A second problem which can arise with prior art apparatus is caused by a capacitive effect where one electrode of the capacitance is the active electrode and the other electrode of the capacitance is a metallic trocar sheath and the dielectric between these elements is the insulation on the active electrode. Current from the active electrode will be capacitively coupled to the trocar sheath and then returned through the body and the return electrode to the generator. If this current becomes concentrated, for example, between the trocar sheath and an organ such as the bowel, the capacitive current can cause a burn to the organ. A third potential problem occurs if the active electrode contacts another instrument within the peritoneal cavity such as metallic graspers or the like. The above-mentioned capacitive effect also arises in this situation where the first electrode is the active electrode and the second electrode is the metallic graspers or the like. Thus, where the grippers contact a unintended site, injury may occur.

To solve some of the above identified problems, an electrosurgical apparatus as disclosed in U.S. Pat. 5,312,401 to Newton et al. and assigned to the assignee of the present invention has been proposed, the contents of which are incorporated herein by reference. Newton et al. disclose an electrosurgical apparatus that includes a safety shield that surrounds an active electrode and that includes insulation provided at least on the outer surface of the shield and preferably also provided on the inner surface of the shield. The safety shield is connected to a return lead via a low impedance path that includes monitoring circuitry used to detect the shield current and determine an abnormal condition therefrom.

In the event that the insulation on the active electrode is damaged, current will pass through the damaged insulation to the shield and then be returned to the return lead via the low impedance electrical connection between the shield and the return lead of the electrosurgical generator. A monitor circuit responsive to the shield current deactivates the electrosurgical generator whenever the shield current corresponds to an abnormal condition such as an insulation breakdown. The insulated shield of Newton et al. also addresses the second and third above-mentioned problems by harmlessly returning any current which is capacitively coupled to the shield to the return lead via the above-mentioned low impedance connection.

Referring to FIG. 1 a cross-sectional view of an illustrative laparoscopic apparatus in accordance with Newton et al. is shown. A tubular safety shield assembly 15 includes a tubular shield 9 having a layer of insulation 11 provided on the outer surface thereof and an optional layer of insulation 13 provided on the inner surface thereof. The tubular shield assembly is inserted through trocar sheath 1 to thereby provide a passageway through which the active electrode probe 3 may be inserted. An elongated port 23 may extend through the active electrode through which irrigation fluids, suction, a pressurized gas stream, etc. may pass. When active probe 3 and tubular shield assembly 15 are in their respective inserted positions as shown in FIG. 1, the shield 9 surrounds the active probe from at least (a) a proximal point 17 prior to the entry point 19 of the active probe into the trocar sheath 1 to (b) a distal point 21 in proximity to the tip 7 of the active probe. Shield monitor circuitry 25 is connected to shield 9 via a dual conductor lead 27 whereby the integrity of the connection of the shield to the monitor circuitry can be monitored.

The active electrode probe 3 is connected to an electrosurgical generator 31 which may be of a conventional type via an active lead 35. The electrosurgical generator is connected to a patient return electrode 37, preferably of the dual area type, via the shield monitor circuitry 25 and, in particular, the return terminal of the generator is connected to circuitry 25 via lead 29 while the circuitry 25 is connected to the return electrode via lead 33. Upon detection of a fault condition by the shield monitor circuitry, the electrosurgical generator 31 may be deactivated by opening a relay in the connection between the generator and patient return electrode 37 although other means may also be employed to deactivate the generator.

Referring to FIG. 2 a generalized block diagram of the shield monitor circuitry 25 shown in FIG. 1 and used in Newton et al. is shown. A conductivity monitor 39 is connected to dual lead 27, the purpose of the conductivity monitor circuit being to measure the integrity of the connection of lead 27 to shield 9. The dual connection provides a redundant path for shield monitoring current which is applied to lead 27 as will be described in more detail hereinafter with respect to FIG. 9. A shield current sensor 41 senses the current passing from the shield 9 to return electrode lead 29, 33 and may provide a signal voltage proportional to the instantaneous value of the shield current.

Measurement electronics circuitry 43 includes various circuits for measuring different parameters of at least the sensed shield current. The first of these circuits is a full bandwidth amplitude sensor circuit 47 which measures the amplitude of the full bandwidth of the sensed shield current. Processing and decision circuitry 53 determines whether this amplitude exceeds a predetermined threshold and, if it does, a fault condition may be applied to indicators 61 over line 55. Indicators 61 may be aural and/or visible and provide an appropriate alert. A data logger 73 may also be connected to processing and decision circuitry 53 to provide a hard copy of various safety conditions.

In addition to applying an alert signal over line 55, a generator deactivate signal is applied over line 69 to a relay 71 which opens the connection between return electrode 37 and generator 31 to thus deactivate the generator and discontinue the application of electrosurgical energy. That is, the monitor circuitry 25, when used outside host electrosurgical generator 31, is preferably used with an electrosurgical generator of the type having a dual return electrode lead whereby the integrity of the return electrode connection can be monitored. Such monitoring circuitry is known whereby a split (or double) patient electrode is employed and a DC current (see German Patent No. 1139927 published Nov. 22, 1962) or an AC current (see U.S. Pat. Nos. 3,933,157 and 4,200,104) is passed between the split electrodes to sense patient contact resistance or impedance between the patient and the electrodes. If an open circuit condition is sensed, the generator is deactivated. Since the relay 71 of FIG. 2 is opened upon detection of a fault condition, the return electrode connection is also opened to thus deactivate the generator. However, it is to be understood other means will also occur to those skilled in this art for deactivating the generator upon detection of a fault condition by monitor circuitry 25.

Relative amplitude measurement circuitry 51 may be responsive to the ratio of the amplitudes of the sensed shield current and the sensed return electrode current as determined by return current sensor 65. Processing and decision circuitry 53 determines whether this ratio exceeds a predetermined threshold and if it does an alert signal is applied over line 55 while a deactivate signal is applied over line 69 to relay 71 in a manner similar to that described above with respect to the absolute amplitude fault condition.

Phase sensing circuitry 75 is responsive to the phase difference between the voltage applied to the active lead 35 of FIG. 1 and the sensed shield current. In FIG. 1 the monitor circuitry 25 is indicated as being housed outside host electrosurgical generator 31. However, it may also be incorporated within the electrosurgical generator. In the latter instance, access may be readily gained to the active voltage and thus the phase comparison made by phase sensing circuitry 75 can be readily effected. When the monitor is located outside of the host electrosurgical unit, it is somewhat more inconvenient to gain access to the applied voltage signal; nonetheless, appropriate means will occur to those of ordinary skill in the art to gain access to this signal.

Detection of the phase difference between the active voltage and the shield current is a particularly good indicator of a fault condition. That is, normal shield currents are exclusively capacitive—in particular, due to the capacitive coupling between active electrode 5 and shield 9, there is a 90° phase difference between the active voltage and the shield current under normal conditions. Hence, as long as the insulation between the active electrode and the shield is intact, a normal condition will be sensed by phase sensing circuitry 75.

In general, the phase sensing circuitry, in response to the phase difference between the applied inputs being 90°, provides a first output (high voltage, for example). If there is an insulation breakdown between the active electrode 5 and the safety shield 9, arcing will typically occur and such arcing currents are almost exclusively in phase with the applied voltage. That is, the shield current will be in phase with the active voltage. Phase sensing circuitry 75 detects this in phase, fault condition to change the output from high to low.

Spectral sensing or filtered bandwidth circuitry 77 provides a further reliable means for detecting the presence of arcing between the active electrode and shield. Moreover, this method does not need access to the active electrode voltage and thus readily lends itself to those monitor circuitry 25 which are located outside the host electrosurgical generator 31. Spectral sensing circuitry is responsive to at least one predetermined bandwidth of the sensed shield current to detect the presence of a shield current produced by arcing where the arcing will typically occur between the active electrode and the shield due to insulation breakdown therebetween.

Both the phase sensing circuitry 75 and the spectral sensing circuitry 77 also apply inputs to processing and decision circuitry 53 in a manner similar to that described above with respect to circuits 47 and 51 whereby the outputs of circuitry 75 and 77 may be utilized to actuate indicators 61 and data logger 73 and deactivate the electrosurgical generator via relay 71. As indicated above, one or more of the sensing circuits 47, 51, 75, and 77 may be independently utilized or utilized in combination to effect the shield monitor function of circuitry 25.

Various measures have been taken in Newton et al. to render the operation thereof fail-safe. For example, if the monitor circuitry 25 is employed outside host electrical generator 31, there is a possibility the user may connect the return electrode directly into the electrosurgical generator rather than through the monitor circuitry 25 as illustrated in FIG. 1. If this occurs, the shield will not be connected to the return electrode lead through a low impedance path, as will be discussed below, and thus monitor circuitry 25 will be inhibited from performing its monitoring function. To provide an alert to the user that the return electrode has been inappropriately directly connected to the generator 31, a shield to ground voltage sensor 49 may be provided, the sensor 49 being responsive to the shield voltage over line 45 via lead 27. The output of shield/ground voltage sensor 49 is applied to processing and decision circuitry 53 where an appropriate indicator 61 is actuated if the return electrode is directly connected to the electrosurgical generator.

If the return electrode is directly connected to the electrosurgical generator, the voltage on the shield will rise to a substantial percentage of the active voltage in view of an open circuit between the shield and the return electrode lead. Hence, whenever the voltage on the shield exceeds a predetermined threshold, an appropriate signal is applied to processing and decision circuitry 53 over line 57 to thereby provide a desired alert.

Furthermore, when the monitor circuitry 25 is provided outside host electrical generator 31, it is desirable in some instances to battery power the monitor circuitry 25. That is, if the monitor circuitry is powered from an operating room electrical outlet, this will entail an additional wire being connected to the monitor circuitry where in some instances it is desirable that the number of wires associated with the electrosurgical apparatus be reduced to a minimum. Accordingly, an activation control unit 59 may be employed which is responsive to the sensed shield current over line 63 or the sensed return current over line 67 to provide a battery power supply for the various circuits of monitor circuitry 25.

However, even with the use of the safety shield as disclosed in Newton et al., additional problems continue to exist when such an apparatus is used in a laparoscopic procedure or the like. Specifically, in order to facilitate sterilization and replacement of electrosurgical instruments, there is a demand for a shielded electrosurgical instrument that accepts a plurality of electrosurgical inserts (such as graspers, scissors, etc.) that can easily be removed and replaced. Furthermore, there is a need for such inserts to be reliably and securely attached to the shielded electrosurgical instrument in order to prevent undesirable loosening during a surgical procedure. However, it is still desirable for the electrosurgical insert to be easily removed to facilitate sterilization of the electrosurgical instrument.

Furthermore, potential problems exist with respect to the interconnection between an electrosurgical generator and a shielded electrosurgical instrument. Although precautions to ensure proper interconnection to the shield of the electrosurgical instrument have been previously taken, there still exists a possibility that a false signal indicating proper interconnection could result. In such case, a surgeon could proceed under the false impression that the shield monitor was operational when in fact it is not. Of course, in the event of an insulation failure, the results could be catastrophic.

Furthermore, the structure of the connectors used to make a connection between the active and shield electrodes of and electrosurgical instrument and an electrosurgical generator and monitor are such that foreign matter, such a liquids encountered during the surgical procedure, could invade the connector housing, thus creating an electrical short circuit between the active electrode and the shield electrode of the electrosurgical instrument. Again, such a situation is undesirable when performing an electrosurgical procedure.

Also, inserts designed for use with electrosurgical instruments are such that a mechanical failure could occur during an electrosurgical procedure, thus rendering the electrosurgical instrument inoperative. Again, should such failure occur during a surgical procedure, danger to the patient could result.

Furthermore, a need exists for an integral shield assembly adapted for use with a plurality of electrosurgical instruments such that the electrosurgical instruments can be selectively interconnected with, and positioned with respect to, the shield assembly. This allows separation of the shield assembly and electrosurgical instrument to be easily accomplished to facilitate sterilization of the instrument. Furthermore, replacement of defective or worn shield assemblies can be easily accomplished with the provision of a standardized shield assembly suitable for use with a plurality of electrosurgical instruments.

SUMMARY OF THE INVENTION

The present invention provides a solution to the above mentioned, and other, problems with prior electrosurgical apparatus and specifically with prior shielded electrosurgical apparatus. In accordance with the present invention, an electrosurgical instrument having a safety shield for use in laparoscopic or like electrosurgical procedures designed to receive a plurality of electrosurgical instrument inserts is disclosed. The electrosurgical inserts are designed so as to provide quick and easy attachment to the electrosurgical apparatus while still providing enhanced resistance to rotation forces encountered during an electrosurgical procedure, and to distribute actuation forces occurring during use. The safety shield includes a crimped portion for transferring forces that occur during operation of an articulating instrument inserted therein to a handle assembly of the electrosurgical instrument. The electrosurgical instrument has a seal that reduces or prevents electrical current from flowing between the active electrode and shield assemblies. The electrosurgical instrument further includes a connector assembly for receiving a mating cable connector and for providing a fail-safe interconnection that is sealed to prevent breakdown between a shield and active conductor of the instrument. A second preferred embodiment of the electrosurgical instrument is adapted to be removably connected with a replaceable shield/connector assembly through which an electrosurgical insert is inserted. Furthermore, positioning of the shield with respect to the electrosurgical insert can easily be accomplished.

In view of the forgoing, it is an object of the present invention to provide an insert for an electrosurgical apparatus having a novel structure that securely attaches the insert to the electrosurgical apparatus.

It is another object of the present invention to provide an insert for an electrosurgical apparatus having a novel structure that permits quick, easy and secure attachment of the insert to the electrosurgical apparatus.

It is a still further object of the present invention to provide an insert for an electrosurgical apparatus having a novel structure that allows for quick and easy replacement of the insert in the electrosurgical apparatus.

It is yet another object of the present invention to provide an insert for an electrosurgical apparatus having a novel structure that can be quickly and easily attached to the electrosurgical apparatus while still providing enhanced resistance to rotation forces encountered during an electrosurgical procedure.

It is a further object of the present invention to provide an insert for an electrosurgical apparatus having a novel interface with the electrosurgical apparatus to redistribute actuation forces applied on that insert during operation.

It is a further object of the present invention to provide an insert for an electrosurgical apparatus having a protrusion that is received by the electrosurgical apparatus and that is used to actuate the electrosurgical insert.

It is another object of the present invention to provide a shield assembly for an electrosurgical instrument that provides a secure interconnection between the shield and associated insulating layers, and the instrument handle assembly to permit actuation force to be more directly transferred to the handle assembly.

It is still another object of the present invention to provide a shield assembly for an electrosurgical instrument that includes a crimped portion for transferring forces that occur during operation of an articulating instrument inserted therein to a handle assembly of the electrosurgical instrument.

It is a further object of the present invention to provide a shielded electrosurgical instrument having improved electrical insulation between the active electrode and shield assemblies.

It is yet another object of the present invention to provide a shielded electrosurgical instrument having a seal that reduces or prevents electrical current from flowing between the active electrode and shield assemblies.

It is another object of the present invention to prevent surface breakdown from occurring between an active electrode and a shield of an electrosurgical instrument.

It is still another object of the present invention to provide an electrosurgical instrument having an improved connector assembly adapted to receive a connector for supplying electrosurgical active potential and for providing interconnection with the electrosurgical instrument shield.

It is another object of the present invention to provide an electrosurgical instrument having an improved connector assembly designed to provide redundant contact points to a shield of the electrosurgical instrument in order to provide for fail-safe operation of that instrument.

It is yet another object of the present invention to provide a cord connector assembly for interconnecting to an electrosurgical instrument and constructed to provide a seal to prevent liquids and other foreign matter from entering the electrosurgical instrument during a surgical procedure.

It is a still further object of the present invention to provide an electrosurgical instrument comprising an integral shield assembly adapted for use with a plurality of electrosurgical instruments such that the electrosurgical instruments can be selectively interconnected with, and positioned with respect to, the shield assembly.

It is an object of the present invention to provide an electrosurgical instrument that includes an integral handle/articulatable instrument assembly that is inserted through an integral shield/connector assembly within the sterile field.

It is an object of the present invention to provide a shield assembly for use with an electrosurgical instrument that can be easily removed and replaced in the event of damage or wear to the shield assembly.

It is an object of the present invention to provide a standardized electrosurgical instrument having a plurality of articulating replaceable/disposable instruments thereon that is adapted for interconnection with a standard, replaceable and/or disposable shield assembly.

It is an object of the present invention to provide an electrosurgical instrument having position means integrally formed therewith to permit position of the electrosurgical instrument with respect to a electrosurgical shield assembly.

BRIEF DESCRIPTION OF THE DRAWINGS

FIG. 5 shows a further enlarged view of an end of the tubular safety shield assembly show in FIGS. 3 and 4.

FIG. 6 illustrates in further detail a portion of an end of the tubular safety shield assembly shown in FIG. 5.

FIG. 7 shows a schematic diagram illustrating the operation of a housing and adapter shown in FIGS. 4–6.

FIG. 8 shows an expanded view of the connector portion and rotatable positioning means of the electrosurgical instrument shown in FIG. 3.

FIG. 14 illustrates an articulatable insert in accordance with the present invention suitable for use with the electrosurgical instrument shown in FIG. 3.

DETAILED DESCRIPTION OF PREFERRED EMBODIMENTS

Figure 1:
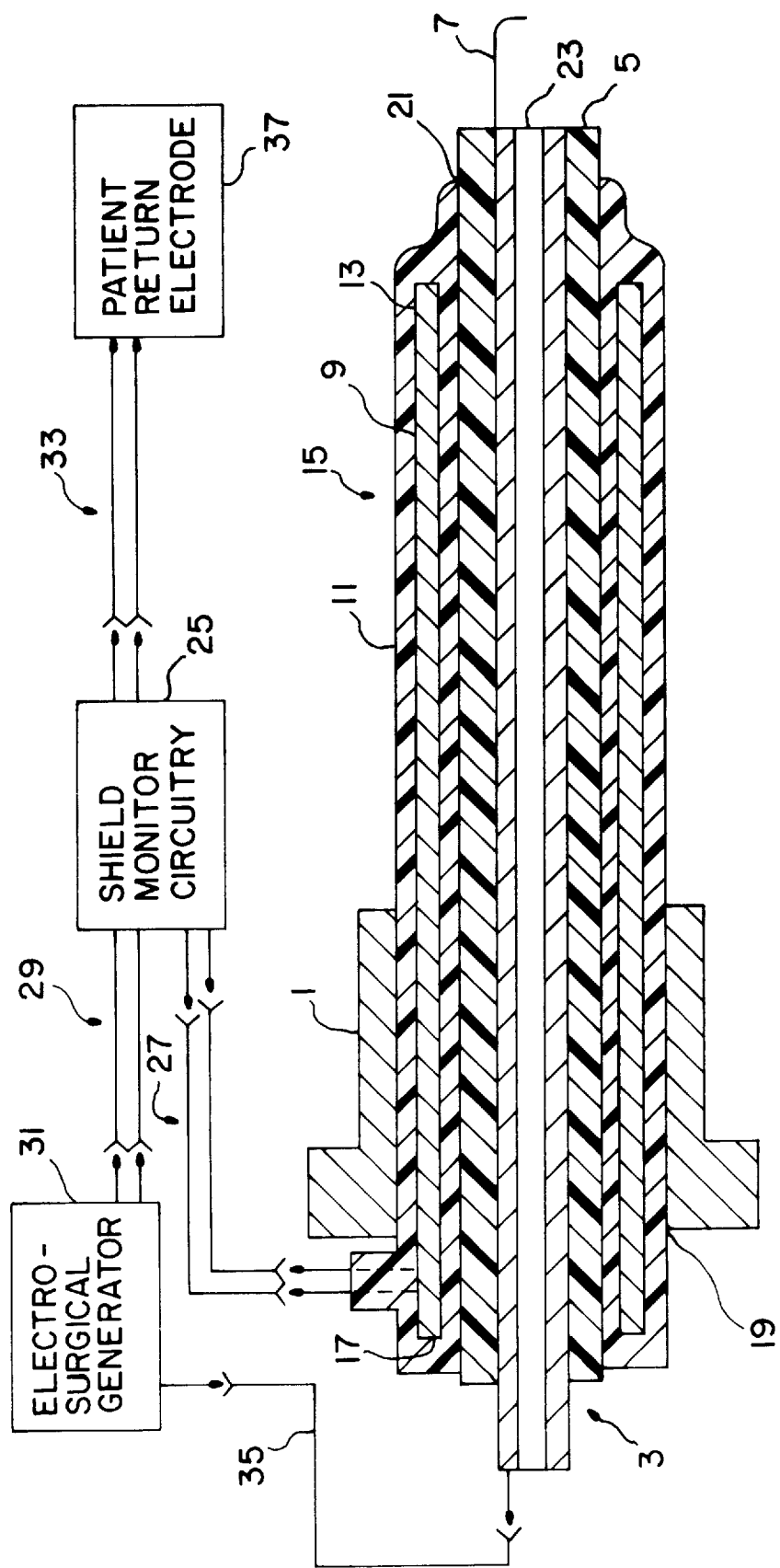
FIG. 1 illustrates a cross-sectional view of a conventional shielded electrosurgical instrument.
Figure 2:
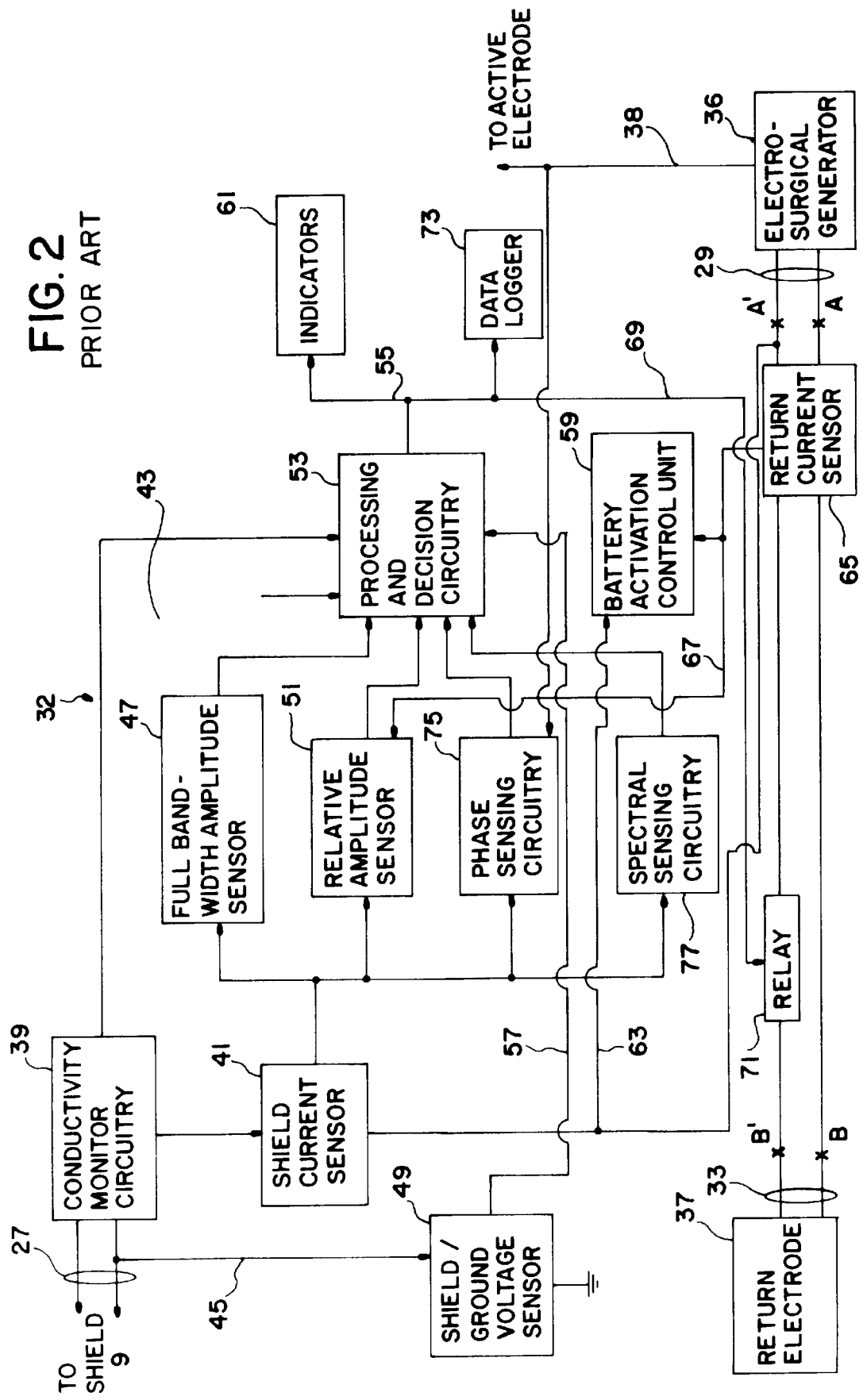
FIG. 2 illustrates a generalized block diagram of conventional shield monitoring circuitry for use with the shielded electrosurgical instrument shown in FIG. 1.
Figure 3:
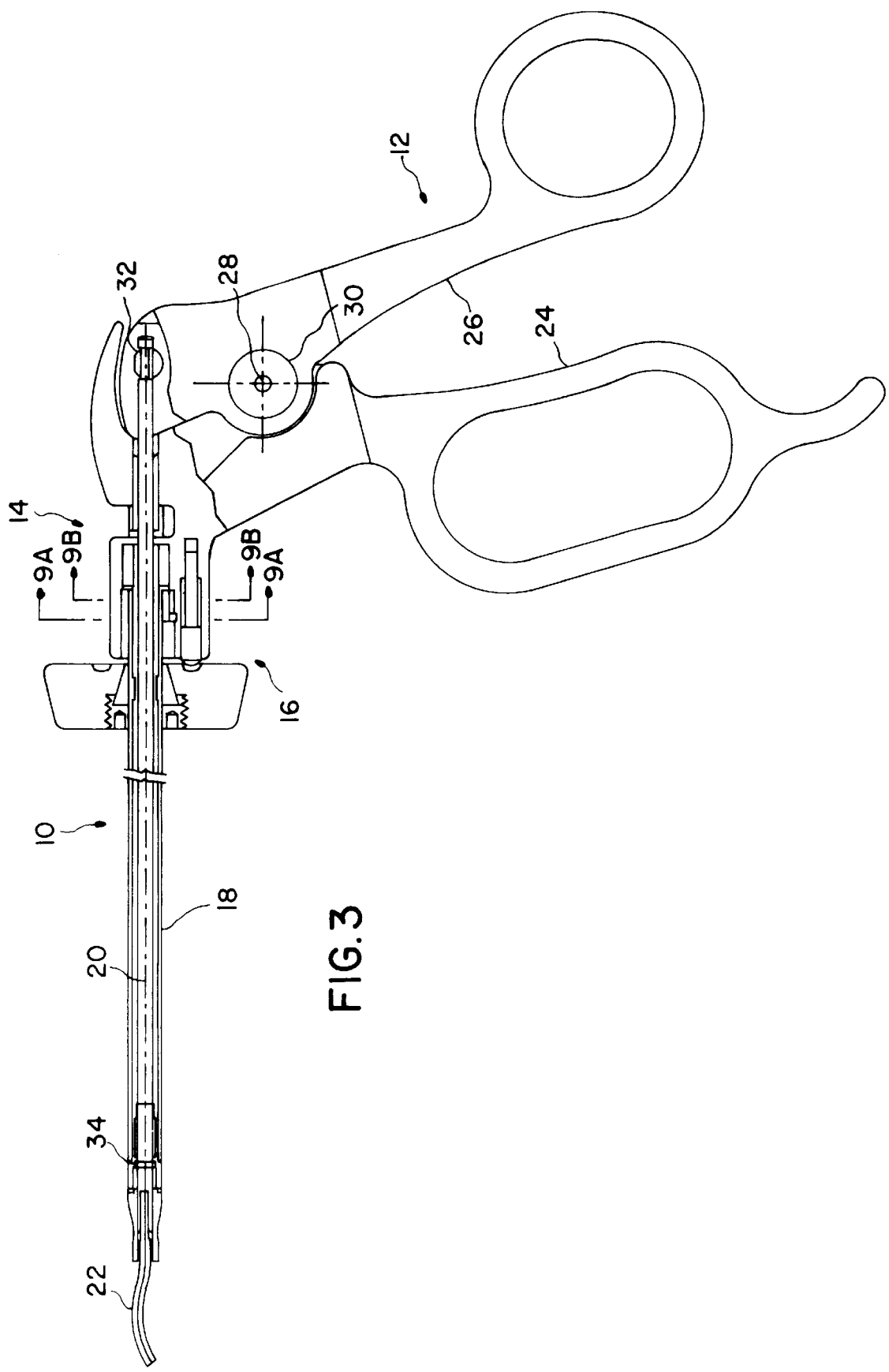
FIG. 3 illustrates an articulated electrosurgical instrument in accordance with the resent invention.

Referring first to FIG. 3, an articulated electrosurgical instrument in accordance with the present invention is shown generally at 10. As can be seen in FIG. 3, the articulated electrosurgical instrument 10 includes a handle assembly 12, a connector portion 14, and a rotatable positioning means 16 disposed at a first end of a tubular safety shield assembly 18. Extending through tubular safety shield assembly 18, is articulated insert 20 that includes articulatable instrument 22 that is disposed at a second end 34 of tubular safety shield assembly 18 as shown in FIG. 3. Although articulatable instrument 22 is shown in FIG. 3 as a scissors, in accordance with the present invention, articulating instrument 22 could be any suitable instrument including scissors, graspers, etc.

Handle assembly 12 includes stationary handle 24 and movable handle 26 that is pivotally attached to stationary handle 24 at pivot point 28 by removable fastener 30. As described in more detail below in connection with FIGS. 14–16, articulating insert 20 extends through stationary handle 24 and removably attaches to a groove in trunnion 32. In this manner, by rotation of movable handle 26 with respect to stationary handle 24 around pivot point 28, articulatable insert 20 can be operated as described below.

Figure 4:
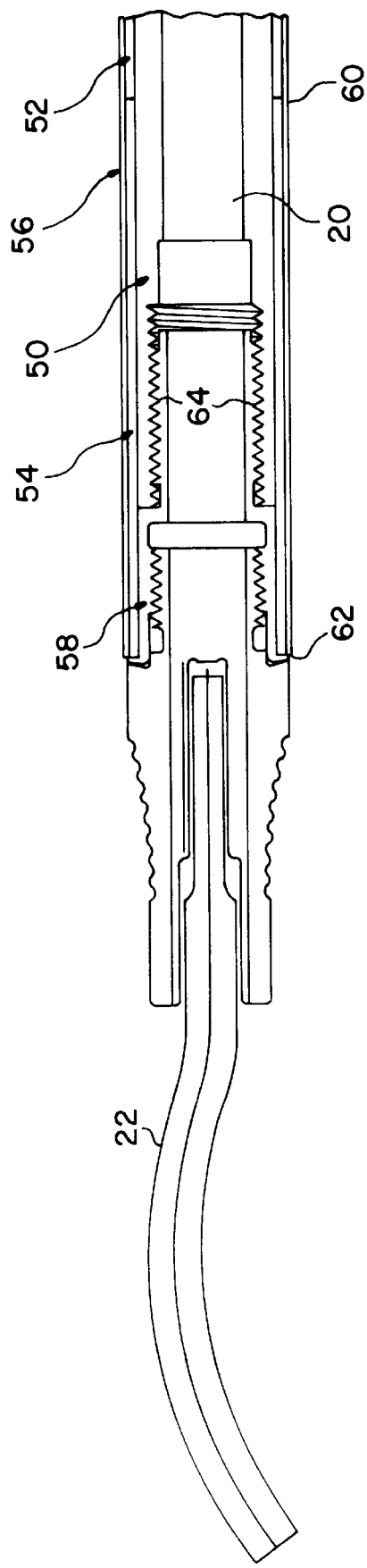
FIG. 4 illustrates an enlarged view of an end of the tubular safety shield assembly shown in FIG. 3.

Articulatable insert 20 is inserted into articulated electrosurgical instrument 10 through second end 34 of tubular safety shield assembly 18. Referring to FIG. 4, an enlarged view of second end 34 of tubular safety shield assembly 18 is shown. As can be seen in FIG. 4, tubular safety shield assembly 18 includes PEEK (Poly-ether-ether-ketone) tube 50, shield 52, inner shrink tube 54, outer shrink tube 56 and adapter 58. Although tube 50 is referred to as being made from PEEK material, any other suitable high temperature insulating material having sufficient structural rigidity could be used instead.

PEEK tube 50 provides the primary structural support for tubular safety shield assembly 18 and serves to insulate articulatable insert 20 from shield 52, which could be, for example, a stainless steel tube. As shown in FIG. 4, shield 52 extends to a point 60 that is in proximity to the end 62 of tubular safety shield assembly 18. Adjacent to shield 52 and extending from point 60 to end 62 of tubular safety shield assembly 18 is inner shrink tube 54 that serves to electrically isolate shield 52 from the exposed surface of articulating instrument 22. Outer shrink tube 56 covers both shield 52 and inner shrink tube 54 and serves to provide additional electrical insulation between shield 52 and the exposed surface of articulating instrument 22. Furthermore, outer shrink tube 56 effectively prevents a conductive material from coming into contact with both shield 52 and articulating instrument 22, thereby creating an electrical short circuit between the shield 52 and articulating instrument 22. Articulating instrument 22 is connected to articulatable insert 20 through appropriate linkages that permits articulatable instrument 22 to be operated by longitudinal motion of articulatable insert 20 through PEEK tube 50. The details of the linkage between articulatable instrument 22 and articulatable insert 20 are conventional and therefore not shown in further detail in FIG. 4.

Adapter 58 is provided in end 62 of tubular safety shield assembly 18 to threadably receive articulatable insert 20. Adapter 58 is used in order to prevent damage from occurring to threads 64 in PEEK tube 50 from repeated attachment and removal of articulatable insert 20 and is preferably made from a more durable material such as metal. In such case, it is important to note that inner shrink tube 54 and outer shrink tube 56 further serve to electrically isolate shield 52 from adapter 58, which in operation will selectively be maintained at an active electrosurgical voltage potential.

FIG. 5 shows a further enlarged view of end 62 of tubular safety shield assembly 18 that contains one particularly important feature of the present invention. For clarity, FIG. 5 includes end 62 of tubular safety shield assembly 18 and adapter 58, but does not show inner shrink tube 54 or outer shrink tube 56, which would be positioned as shown in FIG. 4. As shown in FIG. 5, the connection between articulatable instrument 22 and articulatable insert 20 is formed within housing 70 made from a resilient material sufficient to allow for flexure when a force is exerted at points F1 during insertion of articulatable insert 20.

A further detail of the portion enclosed by circle 72 is shown in FIG. 6. As seen in FIG. 6, housing 70 preferably contacts adapter 58 at end 62 of tubular safety shield assembly 18. Furthermore, as described in more detail below, housing 70 preferably contacts adapter 58 at a point which is on the outer periphery of adapter 58 as shown in FIG. 6. Housing 70 is preferably formed substantially as shown in FIG. 6 so that housing angle 74 between first surface 76 disposed substantially parallel to the longitudinal dimension of articulatable insert 20 and second surface 78 disposed substantially orthogonally to longitudinal dimension of articulatable insert 20 is less than 90°. Similarly, adapter angle 80 is preferably formed so that adapter angle 80 between first surface 82 disposed substantially parallel to the longitudinal dimension of articulatable insert 20 and second surface 84 disposed substantially orthogonally to longitudinal dimension of articulatable insert 20 is less than 90°. Furthermore, it is most preferred that housing angle 74 is less than adapter angle 80. By forming both housing angle 74 and adapter angle 80 less than 90° and by forming housing angle 74 less than adapter angle 80, contact between adapter 58 and housing 70 at the outer periphery of adapter 58 and housing 70 near end 62 is ensured when articulatable insert 20 is secured into tubular safety shield assembly 18.

The specific design of housing 70 and adapter 58 is such that increased frictional forces result when articulatable insert 20 is secured to adapter 58 as described below in connection with FIG. 7. This is desirable in order to increase the amount of rotational force necessary to disengage articulatable insert 20 from tubular safety shield assembly 18 and ultimately from electrosurgical instrument 10. Without the structure shown in FIG. 6 and the associated increase in rotational force necessary to disengage articulatable insert 20, articulatable insert 20 could inadvertently be disengaged from tubular safety shield assembly 18 during a surgical procedure. That is, should a given surgical procedure require that a rotational force be applied to articulating instrument 22, it is important that such force be transferred to the appropriate surgical location and not expended through undesirable rotation between housing 70 (and thus articulatable insert 20 and instrument 22) and adapter 58 (and thus tubular safety shield assembly 18 and electrosurgical instrument 10). Additionally, articulatable insert 20 can easily be securely attached within the sterile field to the electrosurgical instrument during a surgical procedure.

Furthermore, as noted above, the most preferred structure of housing 70 and adapter 58 is such that contact occurs at the outer periphery of housing 70 and adapter 58. This is ensured in the most preferred embodiment by the provision of housing angle 74 and adapter angle 80 both being less than 90° and housing angle 74 being less than adapter angle 80. This is particularly advantageous in that the amount of force required to rotate articulatable insert 20 with respect to tubular safety shield assembly 18 is increased by having the contact point disposed on the outer periphery of housing 70. That is, if the contact point were disposed inward of the outer periphery, the resulting increase in friction would be less than if the contact point were at the outer periphery as shown in FIG. 6.

Referring next to FIG. 7, a schematic diagram of the operation of housing 70 is shown to illustrate the manner in which the design of housing 70 and adapter 58 increase the rotational friction therebetween. As noted above, housing 70 is preferably made from a resilient material sufficient to allow for flexure when a force is exerted at points F1 shown in FIG. 5. When such force is exerted, housing 70 deflects from an at rest position 90, illustrated in FIG. 7 by dotted lines, to a flexed position 92. Furthermore, when such flexure takes place, outer periphery 94 of housing 70 is displaced by a distance 98 with respect to inner periphery 96 of housing 70. Removal of force F1 from housing 70 causes the housing to tend to return to at rest position 90.

From the above description and illustrations shown in FIGS. 5–7, it will be clear to one of skill in the art that the outer periphery of surface 78 of housing 70 near end 62 as shown in FIG. 6 can be laterally displaced away from the outer periphery of surface 84 of adapter 58 near end 62 by exertion of force F1. With the release of force F1, surface 78 will tend to laterally return toward adapter 58 and engage surface 84 of adapter 58 at the outer periphery thereof. Accordingly, during insertion of articulatable insert 20 into tubular safety shield assembly 18, a user can provide force to housing 70 by squeezing the housing at the points indicated by F1. If this force is maintained until articulatable insert 20 is seated in adapter 58, and then released, housing 70 will securely engage adapter 58 as described above and thereby increase the rotational frictional force present between housing 70 and adapter 58. In this manner, one important object of the present invention—the provision of an insert for an electrosurgical apparatus that quickly, easily and securely attaches to the electrosurgical apparatus and which provides enhanced resistance to rotational forces encountered during an electrosurgical procedure—is realized.

Of course, although the above description focuses on adapter 58, it is within the scope of the present invention that adapter 58 need not be present and that end 62 of tubular safety shield assembly 18 be designed to include angle 80 as shown in FIG. 6. In this manner, the same increase in rotational friction can be achieved without the provision of adapter 58 if necessary.

Another important feature of articulatable insert 20 in accordance with a further aspect of the present invention will next be discussed in connection with FIGS. 14–16. FIG. 14 generally illustrates articulatable insert 20 and includes threads 81 which secure articulatable insert 20 with adapter 58 provided in end 62 of tubular safety shield assembly 18. Housing 70, for receiving any one of a plurality of articulatable instruments (not shown) is disposed at a first end 83 of articulatable insert 20.

As noted above in connection with FIG. 3, articulating insert 20 extends through stationary handle 24 and removably attaches to a groove in trunnion 32. In this manner, by rotation of movable handle 26 with respect to stationary handle 24 around pivot point 28, articulatable insert 20 can be operated.

Figure 15C:
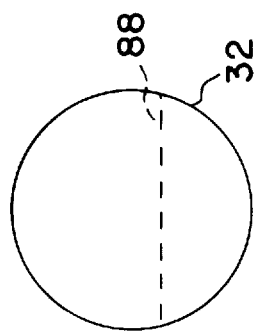
FIG. 15A to 15D illustrates one design in accordance with the present invention for the articulatable insert shown in FIG. 14, and the interaction with the trunnion shown in FIG. 3.
Figure 15D:
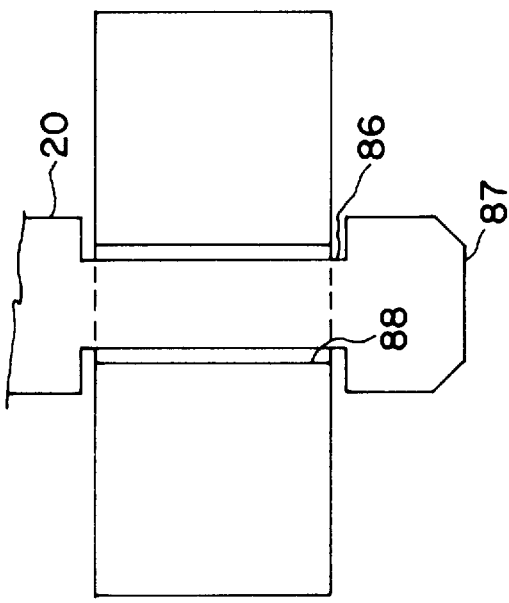
Figure 15A:
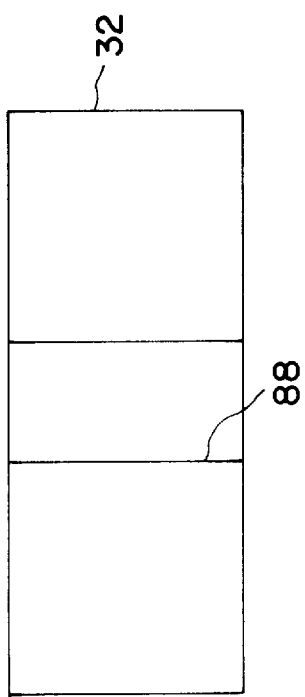
Figure 15B:
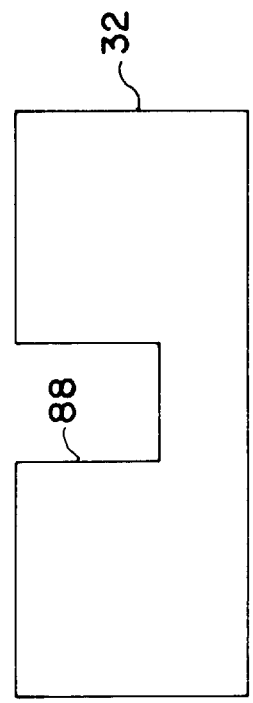

Second end 85 of articulatable insert 20 illustrates a first structure that could be used to interface with the groove in trunnion 32, which is shown in more detail according to one preferred embodiment in FIGS. 15A–15D. FIG. 15A shows a top view of an illustrative trunnion 32 according to the present invention. FIG. 15B shows a front view of trunnion 32 shown in FIG. 15A. FIG. 15C shows a side view of trunnion 32 shown in FIGS. 15A and 15B. Finally, FIG. 15D shows a top view of trunnion 32 similar to FIG. 15A with the articulatable insert 20 inserted therein. As can be seen in FIGS. 14 and 15A–15D, second end 85 of articulatable insert 20 includes a turned down portion 86 and a retaining ball 87. In operation, turned down portion 86 will be inserted into groove 88 in trunnion 32, and retaining ball 87 will cooperate with trunnion 32 to allow the transfer of force from trunnion 32 to articulatable insert 20.

Figure 16C:
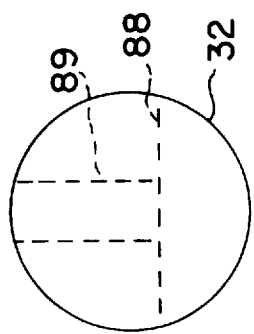
FIG. 16A to 16D illustrate an alternative design in accordance with the present invention for the articulatable insert shown in FIGS. 14 and 15, and the interaction with the trunnion shown in FIG. 3.
Figure 16D:
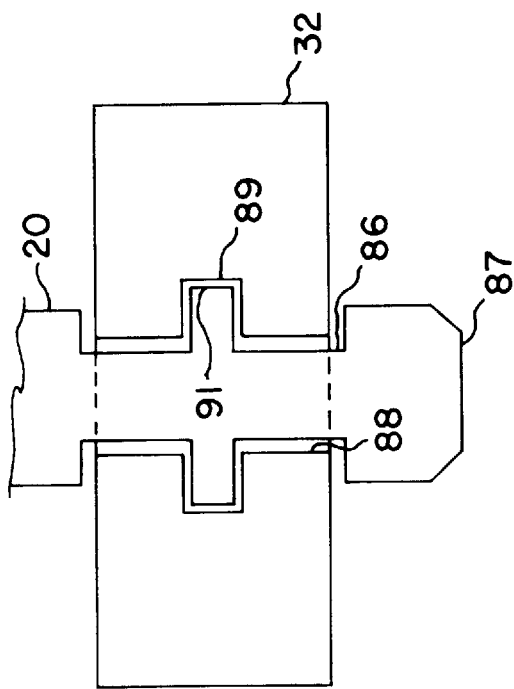
Figure 16A:
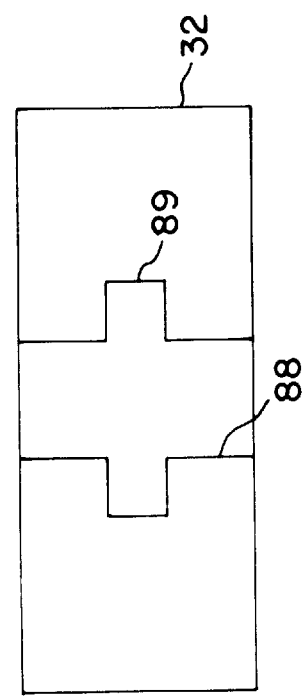
Figure 16B:
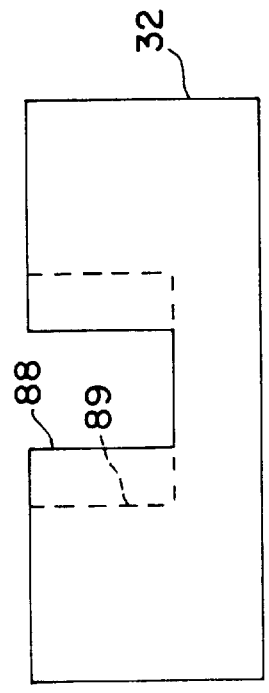

FIGS. 16A–16D show a second preferred structure of trunnion 32 and second end 85 of articulatable insert 20. Again, FIG. 16A shows a top view of trunnion 32 according to this second preferred embodiment, FIG. 16B shows a front view of trunnion 32 shown in FIG. 16A, FIG. 16C shows a side view of trunnion 32 shown in FIGS. 16A and 16B, and FIG. 16D shows a top view of trunnion 32 similar to FIG. 16A with the articulatable insert 20 inserted therein. As can be seen in FIGS. 16A–16D, trunnion 32 includes a notch 89 formed approximately in the center of groove 88 in trunnion 32, and articulatable insert 20 includes protrusion 91. In operation, protrusion 91 is received in notch 89 to provide addition cooperation between articulatable insert 20 and trunnion 32. Accordingly, not only will force be transferred through retaining ball 87 as in the embodiment shown in FIGS. 15A–15D, but also through the interaction of protrusion 91 and notch 89.

In addition to distributing the force applied to articulatable insert 20, protrusion 91 and notch 89 further operate as a fail-safe in the event that retaining ball 87 on second end 85 of articulatable insert 20 is damaged or otherwise becomes non-functional. In such a situation, protrusion 91 and notch 89 will still permit actuation of articulatable insert 20, which could be critical should the failure of retaining ball 87 occur during a surgical procedure.

FIG. 8 shows an expanded cross-sectional view of connector portion 14 and rotatable positioning means 16 as shown in FIG. 3 of electrosurgical instrument 10. As can be seen in FIG. 8, tubular safety shield assembly 18 extends through means 16 and connector portion 14, including PEEK tube 50, shield 52 and outer shrink tube 56. Rotatable positioning means 16 generally includes positioning knob 100, knob locking nut 102, wedge 104 and detent 106. Connector portion 14 generally includes connector housing 110, front seal 112, rear seal 114, ferrule 116, locking ring 118 and active contact electrode 120.

Positioning knob 100 is secured to tubular safety shield assembly 18 through the combination of knob locking nut 102 and wedge 104. Knob locking nut 102 is threadably secured to positioning knob 100 and acts to draw positioning knob 100 to cause a transverse force component to be exerted through wedge 104 to tubular safety shield assembly 18, thus securing positioning knob 100 to tubular safety shield assembly 18. Furthermore, positioning knob 100 includes a plurality of indented portions 122 circumferentially disposed on positioning knob 100 to receive detent 106, which is biased toward positioning knob 100 by spring 124. In this manner, positioning knob 100, and thus tubular safety shield assembly 18 and articulatable instrument 22, can be rotatably positioned at any one of a plurality of positions corresponding to one of indented portions 122 and releasably held in that position by detent 106.

Referring next to connector portion 14, it can be seen that rear seal 114 abuts the rear portion 126 of connector housing 110 and surrounds and is frictionally engaged with PEEK tube 50 and frictionally engaged connector housing 110. In the most preferred embodiment, PEEK tube 50 is machined to a reduced diameter under rear seal 114 in order to improve the surface tolerances and to ensure a uniform frictional engagement between PEEK tube 50 and rear seal 114. That is, during manufacturing the tolerance on the diameter of the PEEK tube is approximately ±0.003 inches, while the tolerance that can be achieved from machining PEEK tube 50 is approximately ±0.001 inches. Silicon grease is also applied to the interface of rear seal 114 with both connector housing 110 and PEEK tube 50 in order to seal any gaps left after rear seal 114 is engaged with PEEK tube 50. Rear seal 114 could be made from any elastomeric electrically insulating material and in the most preferred embodiment is made from tetroflourethylene (TFE).

Rear seal 114 and its interface with PEEK tube 50 are important to prevent an electrical creep path between shield 52 and active contact electrode 120 from occurring. In operation, the active contact electrode 120 of electrosurgical instrument 10 will typically be maintained at a higher voltage potential than shield 52. As can be seen in FIG. 8, this voltage potential will be applied across rear seal 114. In view of this voltage potential, there will be a tendency for current to flow between active contact electrode 120 and shield 52, generally along the interface, or creep path, between rear seal 114 and PEEK tube 50. Such current flow, however, is undesirable since it could lead to a fault condition (as a result of the voltage present on shield 52) and the subsequent deactivation of the electrosurgical generator. Furthermore, should this creep current become too high, the active potential application to the electrosurgical instrument could detrimentally be effected.

In order to reduce this current flow, it is desirable to provide a sufficiently tight, uniform frictional engagement between rear seal 114 and PEEK tube 50. Furthermore, the application of silicon grease, which is also electrically insulating, will further serve to reduce any electrical current flow between active contact electrode 120 and shield 52 along the interface of rear seal 114 and PEEK tube 50. Accordingly, this aspect of the present invention provides an electrosurgical instrument having improved electrical insulation between the active and shield electrodes.

Connector portion 14 further includes ferrule 116, which is attached to shield 52 and in the most preferred embodiment made from metal or other conductive material. As described in more detail below in connection with FIG. 9, ferrule 116 serves to provide an electrical connection between shield 52 and an electrosurgical monitoring apparatus. Ferrule 116 also cooperates with retaining ring 118, which is snap fit into groove 128 in connector housing 110, to secure tubular safety shield assembly 18 into connector housing 110. Finally, front seal 112, which in the most preferred embodiment is made from TFE, is inserted into and frictionally engages connector housing 110 and tubular safety shield assembly 18. Front seal 112 serves to prevent fluid, dirt, or other impurities from entering connector housing 110 and interfering with the connection and operation of retaining ring 118 and ferrule 116.

Another important feature of the present invention shown in FIG. 8 is crimp area 200. PEEK tube 50 has notch 202 circumferentially disposed therein and adapted to receive a portion of shield 52 and outer insulating tube 56 that are crimped at a location corresponding to notch 202. In this manner, shield 52 and outer insulating tube 56 are securely interconnected with PEEK tube 50 to form tubular safety shield assembly 18. This feature is particularly important in that longitudinal actuation forces used to actuate articulating instrument 22 are transmitted from the PEEK tube 50 to the shield 52 through this joint. This in turn transfers a portion of the actuation force to the handle assembly 12 through retaining ring 118, ferrule 116, front seal 112 and rear seal 114. The use of the crimp area 200 is particularly important in permitting this transfer of force while still maintaining electrical isolation between the shield 52 and an articulating insert location within tubular safety shield assembly 18.

Figure 9:
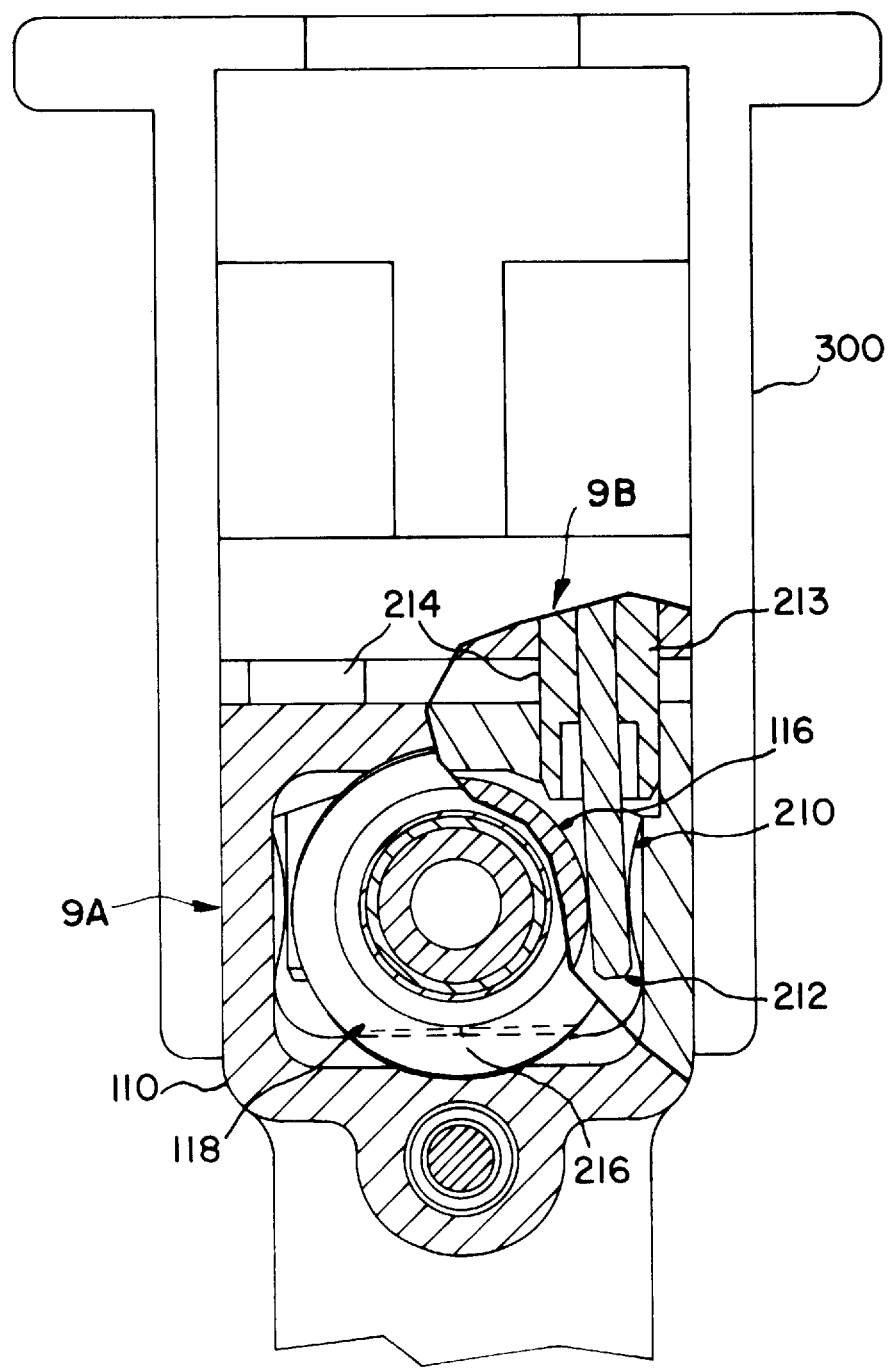
FIG. 9 illustrates a cross-sectional view of the connector portion shown in FIG. 8 taken along the lines A—A and B—B in FIG. 3.

Connector portion 14 is used to provide for electrical connection to both shield 52 and active contact electrode 120, which in turn connects to articulating insert 20 to provide electrosurgical potential to the articulating instrument 22. FIG. 9 illustrates a cross sectional view of connector portion 14 taken along the lines A—A and B—B shown in FIG. 3, and provides further details of the interconnection of shield 52 with a cable leading to an external monitoring apparatus through connector assembly 300. As seen in FIG. 9, connector assembly 300 removably attaches to connector housing 110. Connector assembly 300 preferably includes two contact pins 212 which are received, along with pin insulator 213, in contact holes 214 in connector housing 110.

As can be seen in FIG. 9, connector housing 110 includes contact spring 210, which biases contact pins 212 toward and into contact with ferrule 116. In addition, contact spring 210 makes contact with ferrule 116 at point 216 near the bottom of connector housing 110. This additional contact point ensures that electrical connection between contact pins 212 and ferrule 116 (and thus shield 52) is made. As noted in U.S. Pat. No. 5,312,401 to Newton et al. discussed above, electrosurgical monitoring circuitry detects an electrical interconnection between contact pins 212 in order to determine that connector assembly 300 is properly connected to connector housing 110. That is, if electrical conduction between connector pins 212 is detected, typically as a result of interconnection with ferrule 116 and thus shield 52, then proper connection is indicated.

However, a false indication of proper interconnection could result in the situation where contact pins 212 each come into contact with contact spring 210, but fail to contact ferrule 116. Thus, by virtue of the electrical interconnection through contact spring 210 a proper interconnection would incorrectly be indicated. Accordingly, by providing contact point 216 between ferrule 116 and contact spring 210, should this situation occur, electrical contact between contact pins 212 and shield 52 will still result. Thus, the provision of contact point 216 is particularly advantageous in preventing a false indication that the shield monitoring circuitry is properly connected, which could result in injury to a patient in an electrosurgical procedure.

Figure 10:
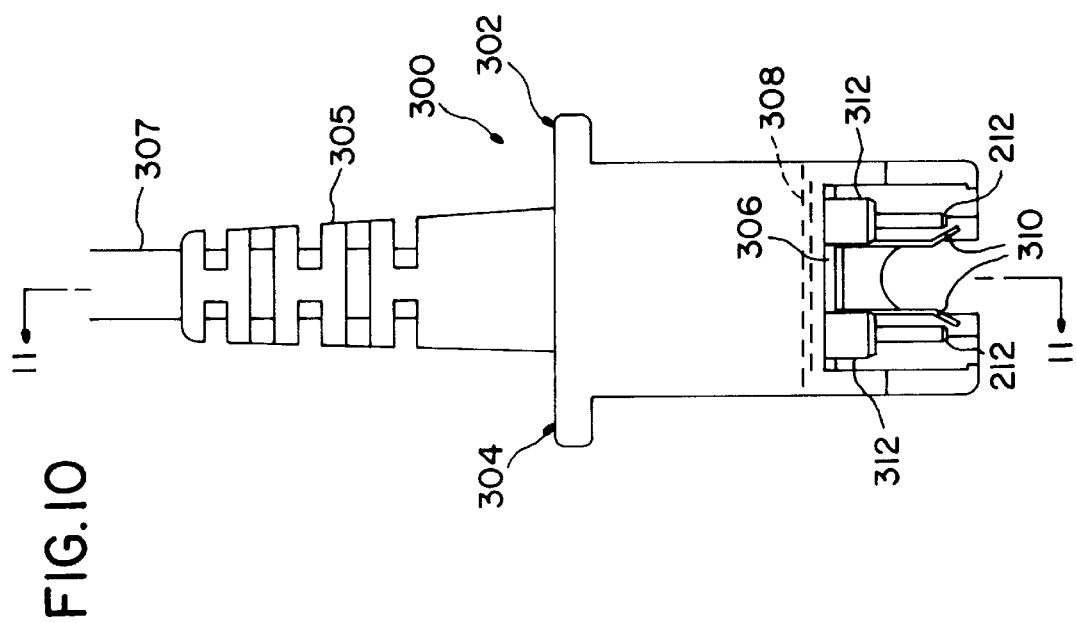
FIG. 10 illustrates an enlarged view of a connector assembly used in accordance with the present invention to interface with the connector portion shown in FIGS. 8 and 9.

Referring next to FIG. 10, an enlarged view of connector assembly 300 is shown. As seen in FIG. 10, connector assembly 300 is formed from plug shells 302, 304 and plug floor 306. Plug shells 302, 304 are held together and to plug floor 306 by screw 308, which extends through plug shell 302, plug floor 306 and is threadably engaged with plug shell 304 to thereby secure plug shells 302, 304 and plug floor 306 together.

Strain relief 305 is provided to reduce the strain on wire 307, which is received by connector assembly 300 to provide electrical contact between connector assembly 300 and electrosurgical generator/monitoring circuitry. Also shown in FIG. 10 are shield contact pins 212 and active contact 310, which serves to connect an active electrosurgical potential received from an electrosurgical generator to electrosurgical instrument 22 through active contact electrode 120, shown in FIG. 8. Also, insulator cups 312 can be seen in FIG. 10 and are described more fully below in connection with FIG. 11.

Figure 11:
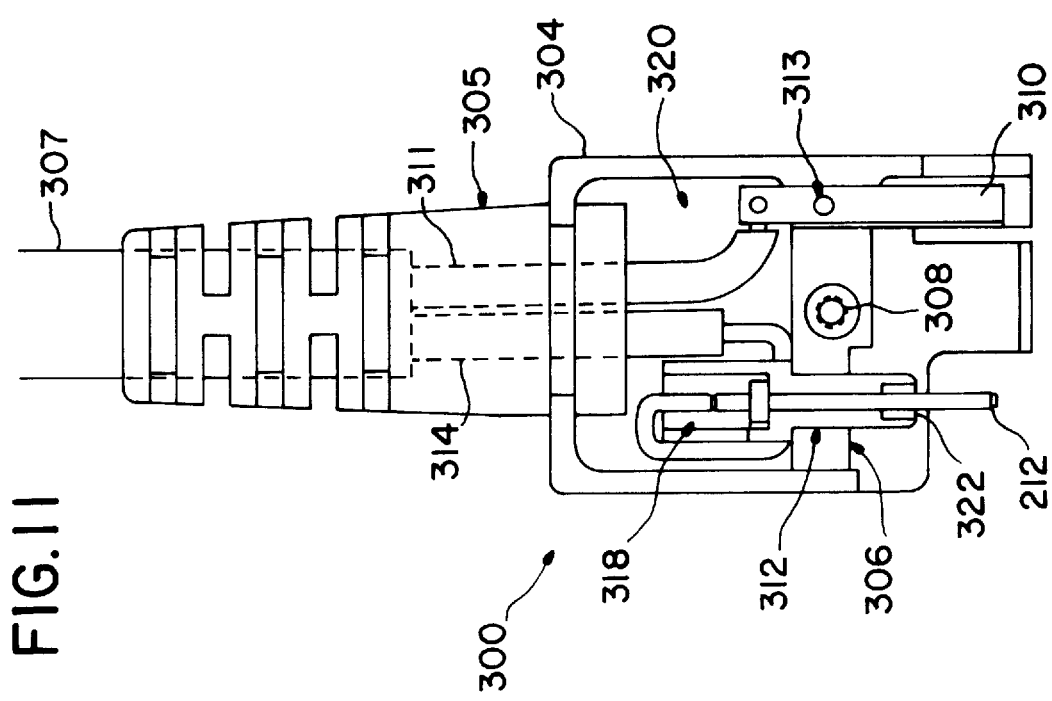
FIG. 11 illustrates a more detailed cross-sectional side view of the connector assembly shown in FIG. 10 taken along line 11—11.

FIG. 11 illustrates a more detailed cross sectional side view of connector assembly 300 taken along line 11—11 in FIG. 10. As seen in FIG. 11, wire 307 includes both active potential supply wire 311 and shield monitor connection wire 314, which are split from wire 307 and connected to active contact 310 and contact pins 212 respectively. Active contact 310 is held in place on plug floor 306 by active contact retaining pin 313.

Importantly, as shown in FIG. 11, contact pins 212 are surrounded by insulator cup 312 as shown. In the most preferred embodiment, insulator cup 312 is made from teflon, or other suitable elastomeric insulating material. Insulator cup 312 includes an upper cavity 318 in which shield monitor connection wire 314 is received and in which connection between shield monitor connection wire 314 and contact pins 212 is made. Preferably, upper cavity 318 is filled with epoxy to secure shield monitor connection wire 314 and to protect the interconnection between shield monitor connection wire 314 and contact pins 212. Additionally, plug cavity 320 is filled with silicon in order to protect and insulate the electrical connections therein.

Insulator cups 312 extend through floor 306 and include lower cavity 322 at an end opposite to upper cavity 318. The lower portion of insulator cups 312 has an outer diameter sufficient to achieve a tight frictional fit with contact holes 214 shown in FIG. 9. In operation, it is important that this fit be sufficient to prevent moisture or other contaminants from entering connector portion 14 through contact holes 214. In this regard, lower cavity 322 is designed to flex inwardly to the extent necessary to allow for insulator cup 312, and therefore contact pins 212, to be tightly engaged with contact holes 214 and therefore connector portion 14. To ensure a sufficiently tight fit, the lower portion of insulator cup 312 near lower cavity 322 may be made to have a diameter slightly larger than that of contact holes 214 such that the lower portion of insulator cup 312 will flex into lower cavity 322 during interconnection with connector portion 14. Also, the particular structure of connector assembly 300 is such that a sealed attachment between the connector assembly and the electrosurgical instrument occurs in order to prevent breakdown between the shield and active electrodes of the electrosurgical instrument.

Figure 12:
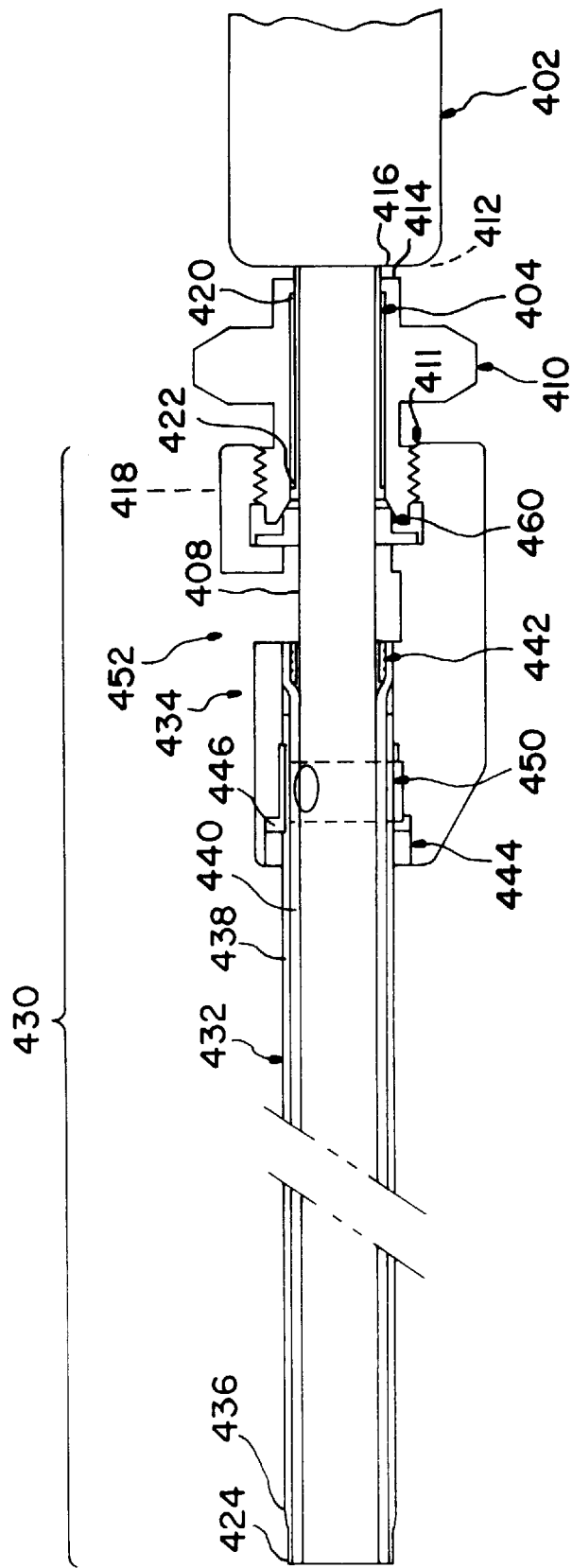
FIG. 12 illustrates an alternative preferred embodiment of an electrosurgical instrument in accordance with the present invention.

An alternative preferred embodiment of the present invention is shown in FIG. 12. The instrument shown in FIG. 12 differs fundamentally from that shown in FIG. 3 in that the electrosurgical instrument shown in FIG. 3 includes an integral handle/shield/connector assembly into which articulatable inserts 20 having articulatable instruments 22 attached thereto are selectively inserted, while the electrosurgical instrument shown in FIG. 12 includes an integral handle/articulatable instrument assembly that is inserted through an integral shield/connector assembly.

Thus, as shown in FIG. 12, this alternative preferred embodiment of the electrosurgical instrument of the present invention includes handle portion 402, active conductor 408 connected to handle portion 402, and docking collar 404 surrounding a portion of active conductor 408 and connected to handle portion 402. Furthermore, locking nut 410 surrounds docking collar 404 and is longitudinally slidable with respect thereto from a point 412, where surface 414 of locking nut 410 contacts surface 416 of handle portion 402, to a point 418, where surface 420 of locking nut 410 contacts surface 422 of docking collar 404. As described in more detail below, this interaction between locking nut 410 and docking collar 404 is particularly important in that it permits active conductor 408 and the associated electrosurgical instrument (not shown) to be precisely positioned within the shield assembly. Locking nut 410 is threadably received by connector portion 434 as indicated generally at 411.

Although not shown in FIG. 12 for clarity, handle portion 402 includes an appropriate user interface, such as illustrated in FIG. 3 by handle assembly 12, which includes stationary handle 24 and movable handle 26. Such user interface operates to slidably articulate an actuation rod disposed within the center of active conductor 408 to operate an articulatable instrument disposed at an opposite end 424 of the electrosurgical instrument shown in FIG. 12. Together, handle portion 402, active conductor 408, docking collar 404 and locking nut 410 form the integral handle/articulating instrument assembly in accordance with this embodiment of the present invention.

Figure 13:
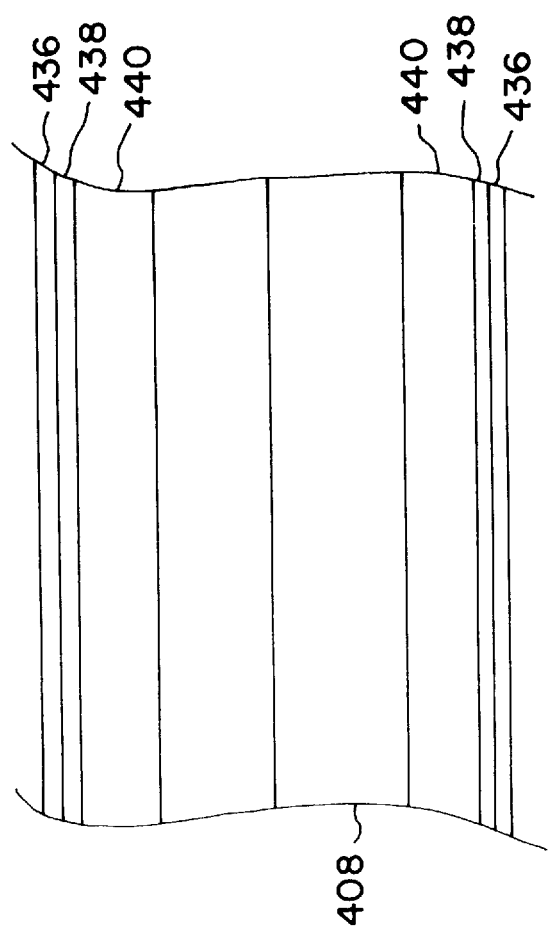
FIG. 13 illustrates an enlarged view of a shield portion of the electrosurgical instrument shown in FIG. 12.

FIG. 12 further depicts an integral shield/connector assembly shown generally at 430. Integral shield/connector assembly 430 further generally includes shield portion 432 and connector portion 434. FIG. 13 shows an enlarged view of shield portion 432, which includes outer insulating layer 436, shield 438 and inner insulating layer 440. In this regard, it will be clear to one of skill in the art that the general structure of shield portion 432 is similar to that illustrated and discussed above in connection with FIG. 4.

As shown in FIG. 12, shield portion 432 is received into connector portion 434. Inner insulating layer 440 extends through a portion of connector portion 434 and is fastened to connector portion 434 by compression ring 442. Outer insulating layer 436 extends into connector portion 434 to a lesser degree and is positioned with respect thereto by seal 444, which frictionally engages connector portion 434 and outer insulating layer 436. Shield 438 extends into connector portion 434 to a point between that of inner insulator 440 and outer insulating layer 436 and is disposed within cavity 446 within connector portion 434.

Connector portion 434 is constructed to allow for interconnection to the shield 438 and active conductor 408 in a manner similar to that discussed above in connection with FIGS. 8–11. Connector portion 434 includes contact spring 450 that is similar in construction and function to contact spring 210 shown in FIG. 9. Access to active conductor 408 is provided in connector portion 434 by way of opening 452, which allows active contact 310 shown in FIGS. 10 and 11 to come into direct contact with active conductor 408. Active contact electrode 120 is not necessary in this embodiment of the present invention in that active conductor 408 is formed to have an appropriate diameter to allow for direct interconnection of active contact 310 thereto.

Connector portion 434 also includes grommet 460 through which active conductor 408 is inserted and which cooperates with locking nut 410 as shown. As is clear from FIG. 12, as locking nut 410 is threaded into connector portion 434, grommet 460 will be forced into contact with active conductor 408 and thus secure active conductor 408 in relation to connector/shield assembly 430.

As discussed above, locking nut 410 surrounds docking collar 404 and is longitudinally slidable with respect thereto from a point 412, where surface 414 of locking nut 410 contacts surface 416 of handle portion 402, to a point 418, where surface 420 of locking nut 410 contacts surface 422 of docking collar 404. Accordingly, when engaged with connector/shield assembly 430, it will be clear that handle portion 402, active conductor 408 and docking collar 404 can be relatively positioned with respect to connector shield assembly 430 and can be secured by tightening of locking nut 410 at any desired relative position. This feature is important in that any instrument, such as articulatable instrument 22, may be selective exposed from end 424 of shield portion 432. Accordingly, more or less of the electrosurgical instrument may be exposed depending on the particular surgical procedure being performed by the release of locking nut 410.

From the forgoing description, it will be clear that the present invention provides numerous improvements to shielded electrosurgical instruments. While the most preferred embodiment of the invention has been described in detail, it will be clear to one of skill in the art that the present invention is not so limited.

What is claimed is:

1. An articulating insert for use with a shielded electrosurgical instrument comprising:
    an elongated rod having first and second ends;
    an articulating instrument connected with said first end of said elongated rod; and
    connection means disposed at said first end of said elongated rod for threadably connecting said elongated rod with the shielded electrosurgical instrument;
    wherein said connection means comprises securing means for securing said articulating insert to the shielded electrosurgical instrument, said securing means operating to increase the rotational friction between the shielded electrosurgical instrument and the articulating insert.

2. The articulating insert of claim 1 wherein said securing means includes a housing having a first surface that engages a second surface of the electrosurgical instrument at an outer periphery thereof, said first surface being formed at a first angle less than ninety degrees from the longitudinal axis of the articulating insert.

3. The articulating insert of claim 2 wherein said second surface of the electrosurgical instrument is formed at a second angle less than ninety degrees from the longitudinal axis of the articulating insert.

4. The articulating insert of claim 3 wherein said first angle is less than said second angle.

5. An electrosurgical instrument comprising:
    a tubular safety shield assembly having a first and second end;
    an elongated articulatable insert received in one of said first and second ends of said tubular safety shield assembly, said insert including an articulatable surgical instrument connected with a first end of said insert; and
    securing means for securing said insert in said tubular safety shield assembly, said securing means operating to increase the rotational friction between said tubular safety shield assembly and said insert.

6. The electrosurgical instrument of claim 5 wherein said tubular safety shield assembly comprises a first tubular member made from an electrically insulating material and an adapter ridgedly received in a first end of said first tubular member.

7. The electrosurgical instrument of claim 6 wherein said first tubular member comprises a PEEK material.

8. The electrosurgical instrument of claim 6 wherein said adapter comprises metal.

9. The electrosurgical instrument of claim 8 wherein said insert is threadably received in said adapter.

10. The electrosurgical instrument of claim 6 wherein said tubular safety shield assembly further comprises:

an electrically conductive shield surrounding an outer periphery of said first tubular member at least in proximity to said first end of said first tubular member;

inner shrink tube insulating means for electrically isolating said electrically conductive shield from said articulatable surgical instrument; and outer shrink tube insulating means for electrically insulating said shield from external conductive components.

11. The electrosurgical instrument of claim 6 wherein said tubular safety shield assembly further comprises:

an electrically conductive shield surrounding an outer periphery of said first tubular member at least in proximity to said first end of said first tubular member;

a first electrical insulator isolating said electrically conductive shield from said articulatable surgical instrument; and a second electrical insulator electrically insulating said shield from external conductive components.

12. The electrosurgical instrument of claim 5 wherein said tubular safety shield assembly includes an adapter ridgedly received in one of said first and second ends and said articulatable surgical instrument is received in a housing that is threadably engaged with said adapter.

13. The electrosurgical instrument of claim 12 wherein said securing means includes a first surface of said housing that engages a second surface of said adapter at an outer periphery thereof.

14. The electrosurgical instrument of claim 13 wherein said first surface is formed at a first angle less than ninety degrees from a longitudinal axis of said tubular safety shield assembly.

15. The electrosurgical instrument of claim 14 wherein said second surface is formed at a second angle, said second angle being less than ninety degrees from the longitudinal axis of said tubular safety shield assembly.

16. The electrosurgical instrument of claim 15 wherein said first angle is less than said second angle.

* * * * *